(12) United States Patent
Mertoglu et al.

(10) Patent No.: US 9,832,991 B2
(45) Date of Patent: Dec. 5, 2017

(54) COMPOSITION CONTAINING A PESTICIDE AND A VINYLIMIDAZOL TERPOLYMER

(75) Inventors: Murat Mertoglu, Ludwigshafen (DE); Stefan Fischer, Freinsheim (DE); Son Nguyen Kim, Hemsbach (DE)

(73) Assignee: BASF SE, Ludwigshafen (DE)

( * ) Notice: Subject to any disclaimer, the term of this patent is extended or adjusted under 35 U.S.C. 154(b) by 88 days.

(21) Appl. No.: 14/009,597

(22) PCT Filed: Apr. 2, 2012

(86) PCT No.: PCT/EP2012/055927
§ 371 (c)(1),
(2), (4) Date: Oct. 3, 2013

(87) PCT Pub. No.: WO2012/136611
PCT Pub. Date: Oct. 11, 2012

(65) Prior Publication Data
US 2014/0031205 A1   Jan. 30, 2014

Related U.S. Application Data

(60) Provisional application No. 61/473,177, filed on Apr. 8, 2011.

(30) Foreign Application Priority Data

Apr. 8, 2011 (EP) .................. 11161673

(51) Int. Cl.
| A01N 25/30 | (2006.01) |
| A01N 47/24 | (2006.01) |
| A01N 43/40 | (2006.01) |
| A01N 57/20 | (2006.01) |

(52) U.S. Cl.
CPC .......... *A01N 25/30* (2013.01); *A01N 43/40* (2013.01); *A01N 47/24* (2013.01); *A01N 57/20* (2013.01)

(58) Field of Classification Search
CPC ........ A01N 43/40; A01N 47/24; A01N 57/20; A01N 2300/00
USPC ......................... 504/100; 514/407
See application file for complete search history.

(56) References Cited

U.S. PATENT DOCUMENTS

| 8,540,974 | B2 | 9/2013 | Braig et al. | |
| 2005/0101724 | A1* | 5/2005 | Kirby et al. | ........ 524/556 |
| 2010/0047203 | A1* | 2/2010 | Dieckmann | ........ A01N 25/30 424/78.18 |
| 2010/0160168 | A1* | 6/2010 | Lindner | ........ A01N 25/02 504/362 |
| 2011/0003956 | A1* | 1/2011 | Kim et al. | ........ 526/263 |
| 2011/0015280 | A1 | 1/2011 | Nguyen Kim et al. | |

FOREIGN PATENT DOCUMENTS

| CA | 2 570 312 | | 1/2006 |
| EP | 2 228 487 | | 9/2010 |
| EP | 2228487 | A1 * | 9/2010 |
| WO | WO 2006/000592 | | 1/2006 |
| WO | WO 2006/018113 | | 2/2006 |
| WO | WO 2007/010034 | | 1/2007 |
| WO | WO 2008/064987 | | 6/2008 |

OTHER PUBLICATIONS

International Search Report, PCT/EP2012/055927, filed Apr. 2, 2012, search completed Jul. 19, 2012.
International Preliminary Report on Patentability, PCT/EP2012/055927, filed Apr. 2, 2012, report completed Mar. 25, 2013.
Declercq, "Pyraclostrobin (210)," (2004), pp. 1007-1118).
Material Safety Data Sheet, "1-Vinylimidazole," Santa Cruz Biotechnology, Inc., (2008), pp. 1-7.

* cited by examiner

*Primary Examiner* — Johann R Richter
*Assistant Examiner* — Courtney Brown
(74) *Attorney, Agent, or Firm* — Brinks Gilson & Lione

(57) ABSTRACT

The present invention relates to an agrochemical composition containing a pesticide and a copolymer, which contains in polymerized form at least 20 wt % vinylimidazol and/or a quaternized vinylimidazol, an acidic comonomer, and a hydrophobic comonomer, which comprises $C_{1-22}$ alkyl (meth)acrylate, mono $C_{1-22}$ alkyl terminated poly(ethylene glycol) (meth)acrylate, vinyl ester of aliphatic $C_{1-32}$ carboxylic acids, or vinyl $C_{1-4}$ alkyl ether. It further relates to a method for preparing said composition by mixing the pesticide and the copolymer; and to a use of said copolymer as dispersing agent in a composition containing a pesticide. In addition it relates to a method for controlling phytopathogenic fungi and/or undesired plant growth and/or undesired attack by insects or mites and/or for regulating the growth of plants, where said composition is allowed to act on the particular pests, their habitat or the plants to be protected from the particular pest, the soil and/or on undesired plants and/or the useful plants and/or their habitat. Finally, it relates to seed containing the said composition.

19 Claims, No Drawings

COMPOSITION CONTAINING A PESTICIDE AND A VINYLIMIDAZOL TERPOLYMER

This application is a National Stage application of International Application No. PCT/EP2012/055927, filed Apr. 2, 2012, which claims the benefit of U.S. Provisional Application No. 61/473,177, filed Apr. 8, 2011, the entire contents of which are hereby incorporated herein by reference. This application also claims priority under 35 U.S.C. §119 to European Patent Application No. 11161673.6, filed Apr. 8, 2011, the entire contents of which is hereby incorporated herein by reference.

The present invention relates to a composition containing a pesticide and a copolymer, which contains in polymerized form vinylimidazol and/or a quaternized vinylimidazol, an acidic comonomer, and a hydrophobic comonomer. It further relates to a method for preparing said composition by mixing the pesticide and the copolymer; and to a use of said copolymer as dispersing agent in a composition containing a pesticide. In addition it relates to a method for controlling phytopathogenic fungi and/or undesired plant growth and/or undesired attack by insects or mites and/or for regulating the growth of plants, where said composition is allowed to act on the particular pests, their habitat or the plants to be protected from the particular pest, the soil and/or on undesired plants and/or the useful plants and/or their habitat. Finally, it relates to seed containing the said composition. Combinations of preferred embodiments with other preferred embodiments are within the scope of the present invention.

Besides the optimization of the active ingredient properties, the development of an effective agent is of particular importance with regard to the industrial production and application of active ingredients. By formulating the active ingredient(s) correctly, an optimal balance must be found between properties, some of which are in conflict with each other, such as the biological activity, the toxicology, potential environmental effects, and the costs. Moreover, the formulation is a decisive factor in determining the shelf life and the user friendliness of a composition.

Agrochemical compositions comprising copolymers are known:

WO 2008/064987 discloses a formulation comprising a pesticide and a copolymer, which contains a) N-vinylamid, such as vinylpyrrolidon, and b) vinylpyrridin, vinylpyrrdidin derivatives or N-vinylimidazol. A use of said copolymer is disclosed for increasing the systemicity of pesticides in formulations.

WO 2006/018113 discloses the use of water-soluble copolymers from (b1) nonionic monoethylenically unsaturated monomers, such as N-vinylpyrrolidon, and (b2) cationic monoethylenically unsaturated monomers, such as N-Vinylimidazol, as thickening agent for aqueous dispersions, for example in agrochemicals.

WO 2006/000592 discloses the use of amphiphilic polymers which contain polyether groups as solubilizers.

US 2005/0101724 discloses an agrochemical formulation comprising an alternating copolymer as dispersant.

Object of the present invention was to find a polymer which allows dispersing a water-insoluble pesticide in aqueous compositions, especially in compositions comprising high concentrations of salts.

The object was solved by an agrochemical composition containing a pesticide and a copolymer, which contains in polymerized form a) at least 20 wt % vinylimidazol and/or a quaternized vinylimidazol, b) an acidic comonomer, and c) a hydrophobic comonomer, which comprises $C_{1-22}$ alkyl (meth)acrylate, mono $C_{1-22}$ alkyl terminated poly(ethylene glycol) (meth)acrylate, vinyl ester of aliphatic $C_{1-32}$ carboxylic acids, or vinyl $C_{1-4}$ alkyl ether.

The copolymer contains vinylimidazol and/or a quaternized vinylimidazol in polymerized form (also called comonomer a)). Preferably, comonomer a) is vinylimidazol ("VI"). In a further preferred embodiment, comonomer a) contains vinylimidazol and a quaternized vinylimidazol.

The imidazolyl moieties of vinylimidazol may be quaternized. The conversion of comonomers a) to quaternary compounds can take place during or, preferably, after the reaction. In the case of a subsequent conversion, the intermediate polymer can be isolated and purified first or converted directly. The conversion can be total or partial. Preferably at least 10%, particularly preferably at least 20% and very particularly preferably at least 30% of the incorporated comonomers (a) are converted to the corresponding quaternary form. Usually up to 99%, particularly preferably up to 90% and very particularly preferably up to 80% of the incorporated comonomers (a) are converted to the corresponding quaternary form.

Preferably at least 10%, particularly preferably at least 20% and very particularly preferably at least 30% of the incorporated comonomers (b) are converted to the corresponding quaternary form. Usually up to 99%, particularly preferably up to 90% and very particularly preferably up to 80% of the incorporated comonomers (b) are converted to the corresponding quaternary form.

Preferably, the comonomers a) are used for the polymerization in predominantly cationogenic form, i.e. more than 70, preferably more than 90, particularly preferably more than 95 and very particularly preferably more than 99 mol % cationogenic, i.e. not in quaternized or protonated form, and only converted to the cationic or protonated form by quaternization during or, particularly preferably, after the polymerization.

In one preferred embodiment of the invention the resulting co-polymer is partially or completely protonated or quaternized only during or, particularly preferably, after the polymerization, because the comonomer a) used for the polymerization is preferably a comonomer that is only partially quaternized or protonated, if at all.

The comonomers a) can either be used in protonated or quaternized form or, preferably, polymerized in unquaternized or unprotonated form, the copolymer obtained in the latter case being either quaternized or protonated during or, preferably, after the polymerization for the use according to the invention.

In the case where the comonomers are used in quaternized form, they can be used either as the dried substance, or in the form of concentrated solutions in solvents suitable for the comonomers, e.g. in polar solvents such as water, methanol, ethanol or acetone, or in the other co-monomer a) provided these are suitable as solvents.

The resulting co-polymers may also be protonated. Examples of compounds suitable for the protonation are mineral acids such as HCl and $H_2SO_4$, monocarboxylic acids, e.g. formic acid and acetic acid, dicarboxylic acids and polyfunctional carboxylic acids, e.g. oxalic acid and citric acid, and any other proton-donating compounds and substances that are capable of protonating the appropriate nitrogen atom. Water-soluble acids are particularly suitable for the protonation.

Possible organic acids which may be mentioned are optionally substituted monobasic and polybasic aliphatic and aromatic carboxylic acids, optionally substituted monobasic and polybasic aliphatic and aromatic sulfonic acids or optionally substituted monobasic and polybasic aliphatic and aromatic phosphonic acids. Preferred organic acids are hydroxycarboxylic acids such as glycolic acid, lactic acid, tartaric acid and citric acid, lactic acid being particularly preferred. Preferred inorganic acids which may be mentioned are phosphoric acid, phosphorous acid, sulfuric acid, sulfurous acid and hydrochloric acid, phosphoric acid being particularly preferred.

The polymer may be protonated either directly after the polymerization or only when the respective pesticide is formulated, during which the pH is normally adjusted to a physiologically acceptable value. Protonation is understood as meaning that at least some of the protonatable groups of the polymer, preferably at least 20, preferably more than 50, particularly preferably more than 70 and very particularly preferably more than 90 mol %, are protonated, resulting in an overall cationic charge on the polymer.

Examples of suitable reagents for quaternizing the compounds a) are alkyl halides having 1 to 24 C atoms in the alkyl group, e.g. methyl chloride, methyl bromide, methyl iodide, ethyl chloride, ethyl bromide, propyl chloride, hexyl chloride, dodecyl chloride, lauryl chloride, propyl bromide, hexyl bromide, octyl bromide, decyl bromide, dodecyl bromide, and benzyl halides, especially benzyl chloride and benzyl bromide. Quaternization with long-chain alkyl radicals is preferably carried out with the corresponding alkyl bromides such as hexyl bromide, octylbromide, decylbromide, dodecyl bromide or lauryl bromide. Other suitable quaternizing agents are dialkyl sulfates, especially dimethyl sulfate or diethyl sulfate. The quaternization of the basic comonomers b) can also be carried out with alkylene oxides such as ethylene oxide or propylene oxide, in the presence of acids. Preferred quaternizing agents are methyl chloride, dimethyl sulfate or diethyl sulfate, methyl chloride being particularly preferred.

The quaternization of the comonomers or polymers with one of said quaternizing agents can be effected by generally known methods.

The acidic comonomer b) may comprise an acidic unit. Preferably, the acidic comonomer comprises a carboxylic acid unit, a sulfonic acid unit, and/or salts thereof. In particular, the acidic comonomer comprises a carboxylic acid unit and/or salts thereof.

Examples of acidic comonomers are acrylic acid, methacrylic acid, vinylsulfonic acid, vinylphosphonic acid, maleic acid, fumaric acid, crotonic acid, itaconic acid, styrenesulfonic acid, vinylsulfonic acid, allylsulfonic acid, methallylsulfonic acid, 2-acrylamido-2-methylpropanesulfonic acid, 2 methacrylamido-2-methylpropanesulfonic acid, 2 acrylamido¬ ethanesulfonic acid, 2-methacrylamidoethanesulfonic acid, 2 acryloxyethane sulfonic acid, 2 methacryloxyethanesulfonic acid, 3-acryloxypropanesulfonic acid, 2-methacryloxypropane sulfonic acid, and/or salts thereof.

If the acidic comonomers are present in their salt form, they have a corresponding cation as counterion. Examples of suitable cations are alkali metal cations, such as $Na^+$ or $K^+$, alkaline earth metal ions, such as $Ca^{2+}$ and $Mg^{2+}$, furthermore ammonium ions, such as $NH_4^+$, tetraalkylammonium cations, such as tetramethylammonium, tetraethylammonium and tetrabutylammonium, furthermore protonated primary, secondary and tertiary amines, in particular those carrying 1, 2 or 3 radicals selected from the group consisting of $C_1$-$C_{20}$-alkyl groups and hydroxyethyl groups, for example the protonated forms of mono-, di- and tributylamine, propylamine, diisopropylamine, hexylamine, dodecylamine, oleylamine, stearylamine, ethoxylated oleylamine, ethoxylated stearylamine, ethanolamine, diethanolamine, triethanolamine or of N,N-dimethylethanolamine.

Most preferred acidic comonomer is acrylic acid and/or methacrylic acid.

The hydrophobic comonomer c) has usually a solubility in water of up to 60 g/l at 20° C., preferably of up to 10 g/l, and in particular of up to 1 g/l.

Suitable examples of hydrophobic comonomers are $C_{1-22}$ alkyl (meth)acrylate, mono $C_{1-22}$ alkyl terminated poly(ethylene glycol) (meth)acrylate, vinyl ester of aliphatic $C_{1-32}$ carboxylic acids, vinyl $C_{1-4}$ alkyl ether, and mixtures thereof. Preferred hydrophobic comonomers are $C_{1-22}$ alkyl (meth)acrylate and mono $C_{1-24}$ alkyl terminated poly(ethylene glycol) (meth)acrylate. In a further preferred embodiment the hydrophobic comonomer comprises $C_{1-22}$ alkyl (meth)acrylate. In a further preferred embodiment the hydrophobic comonomer comprises mono $C_{1-22}$ alkyl terminated poly(ethylene glycol) (meth)acrylate.

Preferred $C_{1-22}$ alkyl (meth)acrylates are linear or branched $C_1$-$C_{22}$-alkyl (meth)acrylates, such as methyl acrylate, methyl methacrylate, ethyl acrylate, n-butyl acrylate, n-hexyl acrylate, n-octyl acrylate, n-decyl acrylate, 2-ethylhexyl acrylat, 2-propylheptyl acrylate, lauryl acrylate, stearyl acrylate, n-hexyl methacrylate, n-octyl methacrylate, n-decyl methacrylate, 2-ethylhexyl methacrylate, 2-propylheptyl methacrylate, lauryl methacrylate and stearyl methacrylat. More preferred are $C_{4-18}$ alkyl (meth)acrylates.

Preferred mono $C_{1-22}$ alkyl terminated poly(ethylene glycol) (meth)acrylate contains 1 to 100, more preferably 3 to 40, and in particular 23 to 30 ethylene glycol moieties. More preferred is mono $C_{12-20}$ alkyl terminated poly(ethylene glycol) (meth)acrylate, in particular mono $C_{15-20}$ alkyl terminated poly(ethylene glycol) (meth)acrylate.

Examples of vinyl esters of aliphatic (linear or branched) $C_{1-32}$ carboxylic acid are vinyl acetate, vinyl propionate, vinyl laurate, vinyl stearate, VeoVa®-10 (vinyl ester of neodecanoic acid) or VeoVa®-9 (vinyl ester of branched $C_{6/7}$ alkyl acid). Preferred vinyl esters of aliphatic $C_{1-32}$ carboxylic acid are vinyl esters of aliphatic $C_{12-24}$ carboxylic acid, such as vinyl laurate and vinyl stearate.

Examples of vinyl $C_{1-4}$ alkyl ether are vinyl methyl ether or vinyl ethyl ether.

The copolymer comprises optionally a hydrophilic comonomer (also called comonomer d)). Usually, the hydrophilic comonomer has a solubility in water of at least 60 g/l at 20° C., preferably of at least 80 g/l and in particular at least 100 g/l.

Examples of hydrophilic comonomer are N-vinyllactams, (meth)acrylamide, poly(ethylene glycol) (meth)acrylate, N—$C_{1-8}$ alkyl acrylamides, and mixtures thereof. Preferred hydrophilic comonomer is N-vinyllactam. Especially preferred hydrophilic comonomer is N-vinylpyrrolidone.

Suitable N-vinyllactams are N-vinyl lactams having 4 to 13 carbon atoms in the lactam ring. Examples are N-vinyl-2-pyrrolidone, N-vinylcaprolactam, N-vinylvalerolactam, N-vinyllaurolactam, N-vinyl-2-piperidone, N-vinyl-2-pyridone, N-vinyl-3-methyl-2-pyrrolidone, N-vinyl-4-methyl-2-pyrrolidone and/or N-vinyl-5-methyl-2-pyrrolidone. It is preferred to use N-vinyl-2-pyrrolidone, N-vinylcaprolactam and/or N-vinyl-2-piperidone. More preferred N-vinyl lactams are N-vinylpyrrolidone, N-vinylcaprolactam or mixtures thereof. Particularly preferred is N-vinylpyrrolidone ("VP").

Preferred poly(ethylene glycol) (meth)acrylates contain 1 to 100, more preferably 3 to 50, in particular 10 to 30, and in most particular 23 to 30 ethylene glycol moieties.

Preferred N—$C_{1-8}$ alkyl acrylamides is N-isopropylacrylamide.

Further comonomers may be present in the copolymer. Usually, less than 5 wt % comonomers are present and preferably no further comonomer is present.

The copolymer comprises usually in polymerized form at least 20 wt %, preferably at least 22 wt %, more preferably at least 25 wt %, and in particular at least 30 wt % vinylimidazol and/or a quaternized vinylimidazol. The copolymer comprises usually in polymerized form up to 80 wt %, preferably up to 70 wt %, more preferably up to 60 wt %, and in particular up to 45 wt % vinylimidazol and/or a quaternized vinylimidazol. In case both vinylimidazol and a quaternized vinylimidazol are present, their amount is added to determine the total concentration of them in the copolymer.

The copolymer comprises usually in polymerized form at least 1.0 wt %, preferably at least 2.0 wt %, and in particular at least 3.0 wt % acidic comonomer (e.g. acrylic acid and/or methacrylic acid). The copolymer comprises usually in polymerized form up to 30 wt %, preferably up to 15 wt %, and in particular up to 7 wt % acidic comonomer (e.g. acrylic acid and/or methacrylic acid).

The copolymer comprises usually in polymerized form at least 1.0 wt %, preferably at least 2.0 wt %, and in particular at least 3.0 wt % hydrophobic comonomer (e.g. $C_{1-22}$ alkyl (meth)acrylate and/or mono $C_{1-22}$ alkyl terminated poly(ethylene glycol) (meth)acrylate). The copolymer comprises usually in polymerized form up to 30 wt %, preferably up to 25 wt %, more preferably up to 15 wt %, and in particular up to 7 wt % hydrophobic comonomer (e.g. $C_{1-22}$ alkyl (meth)acrylate and/or mono $C_{1-22}$ alkyl terminated poly(ethylene glycol) (meth)acrylate).

The copolymer comprises usually in polymerized form at least 5 wt %, preferably at least 10 wt %, more preferably at least 30 wt %, and in particular at least 45 wt % hydrophilic comonomer (e.g. N-vinylpyrrolidone). The copolymer comprises usually in polymerized form up to 75 wt %, preferably up to 70 wt %, and in particular up to 65 wt % hydrophilic comonomer (e.g. N-vinylpyrrolidone).

The copolymer comprises usually in polymerized form at least 20 wt % vinylimidazol and/or a quaternized vinylimidazol, at least 1 wt % acidic comonomer (e.g. acrylic acid and/or methacrylic acid), at least 1 wt % hydrophobic comonomer (e.g. $C_{1-22}$ alkyl (meth)acrylate and/or mono $C_{1-22}$ alkyl terminated poly(ethylene glycol) (meth)acrylate), and optionally at least 5 wt % hydrophilic comonomer (e.g. N-vinylpyrrolidone).

The copolymer comprises usually in polymerized form up to 80 wt % vinylimidazol and/or a quaternized vinylimidazol, up to 20 wt % acidic comonomer (e.g. acrylic acid and/or methacrylic acid), up to 25 wt % hydrophobic comonomer (e.g. $C_{1-22}$ alkyl (meth)acrylate and/or mono $C_{1-22}$ alkyl terminated poly(ethylene glycol) (meth)acrylate), and optionally up to 70 wt % hydrophilic comonomer (e.g. N-vinylpyrrolidone).

Preferably, the copolymer comprises in polymerized form 20 to 80 wt % vinylimidazol and/or a quaternized vinylimidazol, 1 to 20 wt % acidic comonomer (e.g. acrylic acid and/or methacrylic acid), 1 to 25 wt % hydrophobic comonomer (e.g. $C_{1-22}$ alkyl (meth)acrylate and/or mono $C_{1-22}$ alkyl terminated poly(ethylene glycol) (meth)acrylate), and optionally 5 to 70 wt % hydrophilic comonomer (e.g. N-vinylpyrrolidone).

More preferably, the copolymer comprises in polymerized form 20 to 70 wt % vinylimidazol and/or a quaternized vinylimidazol, 1 to 15 wt % acidic comonomer (e.g. acrylic acid and/or methacrylic acid), 1 to 25 wt % hydrophobic comonomer (e.g. $C_{1-22}$ alkyl (meth)acrylate and/or mono $C_{1-22}$ alkyl terminated poly(ethylene glycol) (meth)acrylate), and optionally 10 to 70 wt % hydrophilic comonomer (e.g. N-vinylpyrrolidone).

In general, the wt % of all comonomers (such as a), b), c) and optional monomer d)) add up to 100 wt %.

The copolymer may be prepared by known processes of radical copolymerisation. Suitable processes may be found in WO 2008/064987, WO 2006/018113, WO 2007/010034, DE 10 2005 046 916, or EP 0 913 143.

Typically, the copolymer is a random copolymer or a block copolymer, wherein a random copolymer is preferred.

The composition contains usually from 0.1 to 40 wt % of the copolymer. Preferably, it contains from 1 to 20 wt % of the copolymer, in particular from 3 to 15 wt %, based on the total weight of the composition. In a further embodiment, the composition contains preferably at least 0.2 wt %, in particular at least 0.3 wt % of the copolymer.

The composition according to the invention may be solid or liquid. Preferably it is a liquid. The liquid may be aqueous or non-aqueous.

Preferably the composition is an aqueous composition. The composition often comprises from 5 to 90 wt % water, preferably from 20 to 70 wt %, in particular from 35 to 65 wt %, based on the total weight of the composition. The aqueous composition is may be in form of dispersion, such as an emulsion, suspension or suspoemulsion. Preferably, the composition is an emulsion.

In a preferred embodiment, the composition according to the invention is an aqueous composition which contains the water-insoluble pesticide, the copolymer and optionally a dissolved salt.

The composition (e.g. the aqueous composition) may comprise an organic solvent. Usually, at least one pesticide is dissolved in organic solvent. The organic solvent is preferably emulsified in the aqueous composition. In a preferred embodiment, the organic solvent has a solubility in the aqueous composition of up to 100 g/l at 20° C., preferably of up to 50 g/l, in particular of up to 5 g/l and particularly preferred of up to 1 g/l. In a further preferred embodiment, the organic solvent has a solubility in water of up to 150 g/l at 20° C., preferably of up to 100 g/l, in particular of up to 80 g/l and particularly preferred of up to 60 g/l.

The composition may comprise up to 40 wt %, preferably up to 30 wt % and in particular up to 20 wt % organic solvent, based on the total weight of the composition. In a further embodiment, the composition may comprise from 1 to 40 wt %, more preferably from 5 to 30 wt % organic solvent, based on the total weight of the composition.

Suitable organic solvents are for example mineral oil fractions of medium to high boiling point, such as solvent naphta (e.g. Solvesso® 200), kerosene or diesel oil; coal tar oils and oils of vegetable or animal origin; aliphatic, cyclic and aromatic hydrocarbons, e.g. toluene, xylene, paraffin, tetrahydronaphthalene; alkylated naphthalenes or their derivatives; alcohols such as methanol, ethanol, propanol, butanol, cyclohexanol, benzyl alcohol and o-sec-butyl phenol; glycols; ketones such as cyclohexanone; gammabutyrolactone; fatty acid dimethylamides, such as N,N-dimethyldecanamide (e.g. Agnique® AMD 10), N,N-Dimethyloctanamide/decanamide (e.g. Agnique® AMD 810); fatty acids and fatty acid esters; amines such as N-methylpyrrolidone; ester, such as dibutyl adipate (Agnique® AE 6-4 Di), dimethyl adipate, 2-ethylhexyl lactate (e.g. Agnique® 3-2 EH, Purasolv® EHL); and mixtures of the aforementioned organic solvents. Preferred organic solvents are benzyl alcohol, o-sec-butyl phenol, solvent naphta, N,N-dimethyldecanamide, dibutyl adipate, dimethyl adipate, 2-ethylhexyl lactate, N,N-Dimethyloctanamide/decanamide. Most preferred solvents are benzyl alcohol, o-sec-butyl phenol, and solvent naphta. Mixtures of organic solvents may also be used.

The composition comprises a pesticide. The pesticide can be selected from the group consisting of fungicides, insecticides, nematicides, herbicide and/or safener or growth regulator, preferably from the group consisting of fungicides, insecticides or herbicides. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas. Silver and silver ions are typically not considered as a pesticide.

The composition may comprise from 0.01 to 50 wt % pesticide. Preferably, it comprises from 1 to 20 wt % pesticide.

Preferably, the pesticide comprises at least one water insoluble pesticide. Usually, the pesticide has a solubility in water of up to 10 g/l at 20° C. Preferably, the solubility in water is up to 1 g/l, in particular up to 0.5 g/l.

Preferred water-insoluble pesticides are pyraclostrobin, difenoconazol, metconazole, fluxapyroxad, epoxiconazol, bixafen, preferably pyraclostrobin.

In a preferred embodiment, the composition is an aqueous composition and the pesticide (preferably the water insoluble pesticide) is dispersed in said aqueous composition. The water-insoluble pesticide may be dispersed (e.g. emulsified and/or suspended) in the aqueous composition. The temperature, at which the water-insoluble pesticide is dispersed in the aqueous composition is usually at 20° C. In addition there might be water-insoluble pesticide present partly in dissolved form. Usually, at least 80 wt %, preferably at least 95 wt %, of the water-insoluble pesticide are dispersed (preferably emulsified) in the aqueous composition. Preferably, the water-insoluble pesticide is emulsified in the aqueous composition. When it is emulsified, the pesticide may form the emulsified phase by itself or in mixture with other compounds, such as an organic solvent. In case a further pesticide is present, the water-insoluble pesticide may be emulsified in the aqueous composition, wherein the further pesticide may be dissolved in an organic solvent.

The composition (especially the aqueous composition) may comprises at least one (e.g. one or two) dissolved salt. Preferably, it contains at least 5 wt % of the dissolved salt, more preferably at least 15 wt %, especially preferred at least 25 wt % and most especially preferred at least 35 wt %, based on the total weight of the aqueous composition. Mixtures of dissolved salts may also be present.

Suitable dissolved salts are all compounds which dissociate in water at 20° C. into at least one anion and at least one cation. Examples of dissolved salts are inorganic salts and salts of organic compounds, whereas salts of organic compounds are preferred. More preferably, the dissolved salt contains an ionic pesticide, such as an anionic pesticide or a cationic pesticide. Examples of inorganic salts are alkali, earth alkali, or ammonium salts of sulfate, chloride, sulfonate, carbonate, acetate, or phosphate.

The term "ionic pesticide" refers usually to at least one pesticide, which is present as an ion (e.g. anion or cation) in the aqueous composition according to the invention. Usually, ionic pesticides comprise at least one ionic group, such as an anionic group or a cationic group. Preferably, the ionic pesticide comprises one or two ionic groups. In particular the ionic pesticide comprises exactly one ionic group.

Suitable anionic groups are carboxylate, thiocarboxylate, sulfonate, sulfininate, thiosulfonate or phosphonate groups. A preferred example of an anionic group is a carboxylate group (—C(O)O$^-$). The aforementioned anionic groups may be partly present in neutral form including a protonizable hydrogen. For example, the carboxylate group may be present partly in neutral form of carboxylic acid (—C(O)OH). This is preferably the case in aqueous compositions, in which an equilibrium of carboxylate and carboxylic acid may be present. Mixtures of anionic pesticides may be used.

Suitable anionic pesticides are given in the following. In case the names refer to a neutral form or a salt of the pesticide, the anionic form of the pesticides are meant.

Suitable anionic pesticides are herbicides, which comprise a carboxylate, thiocarboxylate, sulfonate, sulfininate, imidazolinone, thiosulfonate or phosphonate group, especially a carboxylate group. Examples are aromatic acid herbicides, phenoxycarboxylic acid herbicides, imidazolinone herbicides or organophosphorus herbicides comprising a carboxylic acid group.

Suitable aromatic acid herbicides are benzoic acid herbicides, such as chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable imidazolinone herbicides are imazamethabenz, imazamox, imazapic, imazapyr, imazaquin and imazethapyr. Preferred are imazamox and imazapyr.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfopP, isoxapyrifop, metamifop, propaquizafop, quizalofop, quizalofop-P, trifop. Preferred are phenoxyacetic herbicides, especially MCPA.

Suitable organophosphorus herbicides comprising a carboxylic acid group are bilanafos, glufosinate, glufosinate-P, glyphosate. Preferred organophosphorus herbicide is glyphosate.

Suitable other herbicides comprising a carboxylic acid are pyridine herbicides comprising a carboxylic acid, such as fluoroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron.

Suitable anionic pesticides are fungicides, which comprise a carboxylate, thiocarboxylate, sulfonate, sulfininate, thiosulfonate or phosphonate group, especially a carboxylate group. Examples are polyoxin fungicides, such as polyoxorim.

Suitable anionic pesticides are insecticides, which comprise which comprise a carboxylate, thiocarboxylate, sulfonate, sulfininate, thiosulfonate or phosphonate group, especially a carboxylate group. Examples are thuringiensin.

Suitable anionic pesticides are plant growth regulator, which comprise a carboxylate, thiocarboxylate, sulfonate, sulfininate, thiosulfonate or phosphonate group, especially a carboxylate group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

Preferred anionic pesticides are anionic herbicides, more preferably aromatic acid herbicides, phenoxycarboxylic acid herbicides or organophosphorus herbicides comprising a carboxylic acid group, particularly glyphosate.

The aqueous composition may comprise at least one anionic pesticide, such as one, two or three. Preferably, it comprises one.

Suitable cationic groups are amine groups, preferably quaternary amines. Mixtures of cationic pesticides may be used.

Suitable cationic pesticides are given in the following. In case the names refer to a neutral form or a salt of the pesticide, the anionic form of the pesticides are meant.

Examples for cationic pesticides are Atrazine, Simazine, Dodine, Thiram, Manazon, Pyrazon, Ametryne, Prometryne, Benefin, Nitralin, chlormequat and mepiquat.

Preferred cationic pesticide is mepiquat, such as mepiquat chloride or mepiquat pentaborate.

The salt, such as the ionic pesticide, is preferably dissolved in the aqueous composition. The temperature, at which the salt is dissolved in the aqueous composition is usually at 20° C. In addition there might be ionic pesticide present partly in suspended or emulsified form. Usually, at least 80 wt %, preferably at least 95 wt %, of the ionic pesticide are dissolved in the aqueous composition.

The aqueous composition contains usually at least 10 wt % of the salt (e.g. the ionic pesticide), based on the total weight of the composition. Preferably, it contains at least 15 wt %, in particular at least 20 wt %, particularly preferably at least 30 wt % and very particularly preferably at least 35 wt %, based on the total weight of the composition. The composition may comprise up to 70 wt % of the salt (e.g. the ionic pesticide), preferably up to 60 wt %. For the calculation of the wt % of the ionic pesticide, the molecular weight of the anionic pesticide in the form of it ionic form (e.g. as carboxylate) without any counterions is applied.

The aqueous composition may comprise—beside the water-insoluble pesticide and the ionic pesticide—further pesticides.

The compositions according to the invention may also comprise auxiliaries which are customary in agrochemical compositions. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable surface-active substances (adjuvants, wetters, stickers, dispersants or emulsifiers) are the alkali metal, alkaline earth metal and ammonium salts of aromatic sulfonic acids, for example of lingo- (Borresperse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone, and their copolymers.

Surfactants which are particularly suitable are anionic, cationic, nonionic and amphoteris surfactants, block polymers and polyelectrolytes. Suitable anionic surfactants are alkali, alkaline earth or ammonium salts of sulfonates, sulfates, phosphates or carboxylates. Examples of sulfonates are alkylarylsulfonates, diphenylsulfonates, alpha-olefin sulfonates, sulfonates of fatty acids and oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds such as alcohols, alkylphenols, amines (e.g. tallow amine), amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide or of the A-B-C type comprising alkanol, polyethylene oxide and polypropylene oxide. Suitable polyelectrolytes are polyacids or polybases. Examples of polyacids are alkali salts of polyacrylic acid. Examples of polybases are polyvinylamines or polyethyleneamines.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan).

The composition according to the invention can be present in any customary type of agrochemical compositions, e.g. solutions, emulsions, suspensions, dusts, powders, pastes and granules. The composition type depends on the particular intended purpose. Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the composition types (e.g. SC, OD, FS, EC, WG, SG, WP, SP, SS, WS, GF) are employed diluted. Composition types such as DP, DS, GR, FG, GG and MG are usually used undiluted.

Examples for composition types are:
1. Composition Types for Dilution with Water
i) Water-Soluble Concentrates (SL, LS)

10 parts by weight of a pesticide are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a pesticide are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a pesticide are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a pesticide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a pesticide are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a pesticide are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a pesticide are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a pesticide are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition types to be applied undiluted ix) Dustable powders (DP, DS)

5 parts by weight of a pesticide are ground finely and mixed intimately with 95 parts by weight of finely divided kaolin. This gives a dustable composition having an active substance content of 5% by weight.

x) Granules (GR, FG, GG, MG)

0.5 parts by weight of a pesticide is ground finely and associated with 99.5 parts by weight of carriers. Current methods are extrusion, spray-drying or the fluidized bed. This gives granules to be applied undiluted having an active substance content of 0.5% by weight.

xi) ULV solutions (UL)

10 parts by weight of a pesticide are dissolved in 90 parts by weight of an organic solvent, e.g. xylene. This gives a composition to be applied undiluted having an active substance content of 10% by weight.

The present invention further relates to a method for preparing the composition according to the invention by mixing the pesticide and the copolymer. The method may be achieved at temperature from 5 to 100° C., preferably from 10 to 90° C., more preferably from 20 to 80° C. In a further preferred embodiment, the method may be achieved at temperature of at least 40° C.

In order to prepare an aqueous composition comprising an emulsified water-insoluble pesticide, the water-insoluble pesticide is preferably dissolved in the organic solvent and the solution is mixed with an aqueous composition which comprises the copolymer and optionally a salt, such as an ionic pesticide.

In order to prepare an aqueous composition comprising a suspended water-insoluble pesticide, the copolymer is mixed with the aqueous composition optionally comprising the salt (e.g. ionic pesticide), and then the water-insoluble pesticide is suspended therein (e.g. by bead milling).

In order to prepare an aqueous composition comprising a first emulsified water-insoluble pesticide and a second suspended water-insoluble pesticide, both aforementioned methods may be combined. The organic solvent used to prepare this suspoemulsion should be a bad solvent for the suspended pesticide, and a good solvent the emulsified pesticide that is dissolved in it.

The present invention further relates to a method for controlling phytopathogenic fungi and/or undesired plant growth and/or undesired attack by insects or mites and/or for regulating the growth of plants, where the composition according to the invention is allowed to act on the particular pests, their habitat or the plants to be protected from the particular pest, the soil and/or on undesired plants and/or the useful plants and/or their habitat. The agrochemical composition according to the invention may be very useful for the method for controlling phytopathogenic fungi and/or undesired plant growth and/or undesired attack by insects or mites and/or for regulating the growth of plants.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, suspensions, dispersions, emulsions, oil dispersions, by means of spraying, atomizing, dusting, spreading, brushing, immersing or pouring. The application forms depend entirely on the intended purposes; it is intended to ensure in each case the finest possible distribution of the pesticides. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances (also called pesticide) applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300° and Lutensol ON 30®; EO/PO block polymers, e.g. Pluronic RPE 2035° and Genapol B®; alcohol ethoxylates such as Lutensol XP 80®; and dioctyl sulfosuccinate sodium such as Leophen RA®.

The invention also relates to a use of the copolymer as dispersing agent in a composition (preferably an aqueous composition) containing a pesticide (preferably a water-insoluble pesticide). The dispersing agent increases usually the storage stability of the aqueous composition. Preferably, the storage stability of the water-insoluble pesticide is increased, which may be present in emulsified and/or suspended form in the aqueous composition. Storage stability means that the degree of phase separation is visibly reduced upon storage (e.g. when stored at 20° C. for two weeks). Preferably, less coalescence, sedimentation or flocculation of the water-insoluble pesticide may be found upon storage.

The present invention has various advantages: The copolymer has excellent capabilities for dispersing (e.g. emulsifying) water-insoluble pesticides in aqueous compositions, especially when the composition has a high concentration of salts, such as ionic pesticides. The invention enables the preparation of stable fluid pesticides concentrates, especially with high concentrations of ionic pesticides, which could not be prepared with conventional dispersing agent. It is also now possible to combine a high concentration of an ionic pesticide and a water-insoluble pesticide in one aqueous formulation. This combination of pesticides makes the handling easier for farmers: they have to use a single agrochemical formulation instead of several separate ones, and they have to meter only a single formulation instead of two or more separate formulations, and finally this provides additional logistic advantages. Earlier combinations of a high concentration of an ionic pesticide and a water-insoluble pesticide in one formulation were only achieved in dry, dusty agrochemical formulation, which can now be avoided by non-dusty aqueous formulations.

EXAMPLES

Solvesso® 200 ND: Hydrocarbon fluid, aroamtic content>99%, initial boiling point about 242° C., final boiling point about 299° C., commercially available from Exxon Mobile.
Dispersant A: Ammonium salt of polyarylphenylethersulfate.
Dispersant B: 2-Ethylhexyl glucopyranoside.
Comonomers a):
VI: vinylimidazol
QVI: quaternized vinylimidazol (quaternized with gaseous methyl chloride)
Acidic Comonomers b):
MAS: methacrylic acid
Hydrophobic comonomers c):
nBA: n-butyl acrylate
LA: lauryl acrylate, comprising 50-75 wt % dodecyl acrylate and 25-50 wt % tetradecyl acrylate.
2-PHA: 2-propylheptyl acrylate
LUMA: acrylic acid ester of linear C16/18 fatty alcohol terminated poly(ethylene glycol) with about 25 mol ethylene glycol units per molecule.
PEGMA: Monomethyl poly(ethylene glycol) methacrylate, mol weight of PEG was about 350 g/mol
Hydrophilic Comonomers d):
VP: N-vinyl pyrrolidone Example 1—Composition of Polymers The following copolymers were prepared with a composition of comonomers as described in Tables 1 to 3 by precipitation polymerisation or polymerisation in solution according to known methods (e.g. described in WO 2007/010034, DE 10 2005 046 916, or EP 0 913 143).

TABLE 1

Composition of polymers (all values in wt %), prepared by precipitation polymerisation.

| No. | VI | QVI | MAS | LA | nBA | LUMA | VP |
|---|---|---|---|---|---|---|---|
| 1 | 70 | — | 10 | — | 20 | — | — |
| 2 | 25 | — | 5 | — | 20 | — | 50 |
| 3 | 25 | — | 5 | 10 | — | — | 60 |
| 4 | 35 | — | 5 | — | — | 5 | 55 |
| 5 | 30 | — | 7.5 | — | — | 7.5 | 55 |
| 6 | 20 | — | 5 | — | — | 5 | 70 |
| 7 | 25 | — | 5 | — | 20 | — | 50 |
| 8 | 70 | — | 5 | — | 20 | 5 | — |
| 9 | 60 | — | 5 | — | 20 | 5 | 10 |
| 10 | 40 | — | 5 | — | 20 | 5 | 30 |
| 11[a] | 9 | 27 | 3.6 | — | — | 3.6 | 56.8 |
| 12 | 9 | 27 | 3.6 | — | — | 3.6 | 56.8 |

[a]including 0.1 wt % PETAE (pentaerythritol ally ether).

TABLE 2

Composition of polymers (all values in wt %), prepared by solution polymerisation.

| No. | VI | QVI | MAS | LUMA | VP |
|---|---|---|---|---|---|
| 13 | 30 | — | 7.5 | 7.5 | 55 |
| 14 | 30 | — | 7.5 | 7.5 | 55 |
| 15 | 30 | — | 5 | 5 | 60 |
| 16 | 15 | 20 | 5 | 5 | 55 |
| 17 | 20 | — | 15 | 5 | 60 |
| 18 | 20 | 10 | 5 | 5 | 60 |
| 19 | 10 | 20 | 5 | 5 | 60 |
| 20[a] | 20 | — | 5 | 5 | 70 |
| 21[a] | 20 | 10 | 5 | 5 | 60 |

[a]including 0.05 wt % PETAE.

TABLE 3

Composition of polymers (all values in wt %).

| No. | VI | MAS | 2-PHA | LUMA | PEGMA | nBA | VP |
|---|---|---|---|---|---|---|---|
| 22 | 20 | 5 | — | 5 | — | — | 70 |
| 23 | 70 | 5 | — | 5 | — | — | 20 |
| 24 | 70 | 2.5 | — | 2.5 | — | — | 25 |
| 25 | 60 | 2.5 | — | 2.5 | — | — | 35 |
| 26 | 20 | 5 | — | 5 | — | 5 | 65 |
| 27 | 45 | 5 | 10 | — | — | — | 40 |
| 28 | 30 | 5 | 15 | — | — | — | 50 |
| 29 | 20 | 5 | 15 | — | — | — | 60 |
| 30 | 10 | 5 | 15 | — | — | — | 70 |
| 31 | 10 | 5 | 20 | — | — | — | 65 |
| 32 | 45 | 5 | 10 | — | — | — | 40 |
| 33 | 45 | 5 | 10 | — | — | — | 40 |
| 34 | 40 | 10 | 10 | — | — | — | 40 |
| 35 | 25 | 25 | 10 | — | — | — | 40 |
| 36 | 10 | 40 | 10 | — | — | — | 40 |
| 37 | 25 | 25 | 10 | — | — | — | 40 |
| 38 | 45 | 5 | 10 | — | 3 | — | 37 |
| 39 | 45 | 5 | 10 | — | 6 | — | 34 |
| 40 | 45 | 5 | 10 | — | 9 | — | 31 |

Example 2—Preparation of Agrochemical Formulations A to C

The Compositions 1) and 2) were prepared as follows:
Composition 1): Glyphosate isopropylamine salt solution (67.5 wt %, corresponding to about 50 wt % glyphosate free acid), or Roundup® Ultramax (aqueous solution comprising 51 wt % glyphosate isopropylamin salt and 7.5% ethoxylated amine, CAS no. 68478-96-6) was mixed with water and polymer from example 1 and optionally Dispersant A and Dispersant B, and the mixture was intensively mixed for an hour with a dissolver disc.

Composition 2): Pyraclostrobin was dissolved in benzylalcohol or in Solvesso® 200 ND.

The Composition 1) and Composition 2) were mixed. The final mixture was intensively mixed at 50° C. for 1 hour with a dissolver disc until a homogeneous emulsion was obtained. The final composition of the formulations A to C is summarized in Table 4. Samples were taken for storage tests (Example 3). In total 15 formulations of each Formulation A-C were prepared with the polymer no. 1-15 according to Table 1 and 2.

TABLE 4

Composition of formulations A to C with each polymer no 1-15

| Formulation | A | B | C |
|---|---|---|---|
| Glyphosate isopropylamine salt solution | 70% | — | 70% |
| Roundup ® Ultramax | — | 70% | — |
| Polymer from Example 1 | 2% | 2% | 2% |
| Dispersant A | 5% | — | — |
| Dispersant B | 3% | — | — |
| Solvesso ® 200 ND | — | 16% | 16% |
| Benzylalcohol | 16% | — | — |
| Pyraclostrobin | 3.2% | 3.2% | 3.2% |
| Water | up to 100% | up to 100% | up to 100% |

Example 3—Storage Stability

The formulations of example 2 were stored for seven days at 40° C. without moving them. Afterwards, they were visually inspected for phase separation (Table 5 and 6; "Stable" indicates that no phase separation was found).

TABLE 5

Storage stability for polymers of Table 1 and 2. The first column represents the number of the polymer sample as indicated in Table 1 and 2 (n.d.: not determined).

| Polymer No. | Formulation A | Formulation B | Formulation C |
|---|---|---|---|
| 1 | Stable | n.d. | Stable |
| 2 | Stable | n.d. | Stable |
| 3 | Stable | n.d. | Stable |
| 4 | Stable | n.d. | Stable |
| 5 | Stable | n.d. | Stable |
| 6 | n.d. | n.d. | Stable |
| 7 | n.d. | n.d. | Stable |
| 8 | n.d. | n.d. | Stable |
| 9 | n.d. | n.d. | Stable |
| 10 | n.d. | n.d. | Stable |
| 11 | Stable | Stable | Stable |
| 12 | Stable | Stable | Stable |
| 13 | Stable | Stable | n.d. |
| 14 | Stable | Stable | n.d. |
| 15 | Stable | Stable | n.d. |

TABLE 6

Storage stability for polymers of Table 3. The first column represents the number of the polymer sample as indicated in Table 3 (n.d.: not determined).

| Polymer No. | Formulatin A | Formulation B |
|---|---|---|
| 22 | stable | n.d. |
| 23 | stable | n.d. |
| 24 | stable | n.d. |
| 25 | stable | n.d. |
| 26 | stable | stable |
| 27 | stable | n.d. |

TABLE 6-continued

Storage stability for polymers of Table 3. The first column represents the number of the polymer sample as indicated in Table 3 (n.d.: not determined).

| Polymer No. | Formulatin A | Formulation B |
|---|---|---|
| 28 | stable | n.d. |
| 29 | stable | n.d. |
| 31 | n.d. | stable |
| 32 | stable | stable |
| 33 | stable | stable |
| 34 | stable | n.d. |
| 35 | stable | n.d. |
| 37 | stable | n.d. |
| 38 | stable | stable |
| 39 | stable | stable |

Example 4—Preparation of Agrochemical Formulation D to G

The Compositions 3) and 4) were prepared as follows:

Composition 3): The polymer from Example 1 were dissolved in water and Pesticide Solution A (an aqueous solution containing 10 wt % mepiquat chloride and 31 wt % of a dissolved ionic pesticide). The mixture was intensively mixed for an hour with a dissolver disc.

Composition 4): Pyraclostrobin was dissolved in N,N-dimethyldodecanamide, Solvesso® 200 ND, benzyl alcohol or 2-ethyxlhexyl-(5)-lactate.

The Composition 3) and Composition 4) were mixed. The final mixture was intensively mixed at 50° C. for 1 hour with a dissolver disc until a homogeneous emulsion was obtained. The final composition of the formulations D to G is summarized in Table 7. Samples were taken for storage tests (Example 5). Formulations of each Formulation D-G were prepared with the polymers according to Tables 1-3.

TABLE 7

| Formulation | D | E | F | G |
|---|---|---|---|---|
| Pesticide Solution A | 70% | 70% | 70% | 70% |
| Polymer from Example 1 | 2% | 2% | 2% | 2% |
| Solvesso ® ND 200 | 16% | — | — | — |
| N,N-Dimethyldodecanamide | — | 16% | — | — |
| 2-Ethyxlhexyl-(S)-lactate | — | — | 16% | — |
| Benzyl alcohol | — | — | — | 16% |
| Pyraclostrobin | 3.2% | 3.2% | 3.2% | 3.2% |
| Water | up to 100% | up to 100% | up to 100% | up to 100% |

Example 5—Storage Stability

The formulations of example 4 were stored for seven days at 40° C. without moving them. Afterwards, they were visually inspected for phase separation.

TABLE 8

Storage stability for polymers of Table 1 and 2. The first column represents the number of the polymer sample as indicated in Table 1 and 2 (n.d.: not determined).

| Polymer No. | Formulation D | Formulation E | Formulation F |
|---|---|---|---|
| 11 | Stable | Stable | Stable |
| 12 | Stable | Stable | Stable |

TABLE 9

Storage stability for polymers of Table 3. The first column represents the number of the polymer sample as indicated in Table 3 (n.d.: not determined).

| Polymer No. | Formulation G |
|---|---|
| 26 | stable |
| 32 | stable |
| 33 | stable |
| 35 | stable |
| 37 | stable |
| 38 | stable |
| 39 | stable |
| 40 | stable |

We claim:

1. An agrochemical aqueous composition comprising a pesticide and a copolymer comprising
    a) at least 20 wt % vinylimidazol and/or a quaternized vinylimidazol,
    b) an acidic comonomer, and
    c) up to 30 wt % of a hydrophobic comonomer, which comprises $C_{1-22}$ alkyl (meth)acrylate, mono $C_{1-22}$ alkyl terminated poly(ethylene glycol) (meth)acrylate, vinyl ester of aliphatic $C_{1-32}$ carboxylic acids, or vinyl $C_{1-4}$ alkyl ether,
wherein the pesticide is at least 80% dispersed in the aqueous composition and has a solubility in water of up to 10 g/l at 20° C., and
wherein the composition comprises at least 5 wt % of a dissolved salt.

2. The composition according to claim 1, wherein the acidic comonomer comprises a carboxylic acid unit, a sulfonic acid unit or a salt thereof.

3. The composition according to claim 1, wherein the acidic comonomer is acrylic acid or methacrylic acid.

4. The composition according to claim 1, wherein the copolymer comprises
    a) 20 to 80 wt % vinylimidazol or a quaternized vinylimidazol,
    b) 1 to 20 wt % acidic comonomer, and
    c) 1 to 25 wt % hydrophobic comonomer.

5. The composition according to claim 1, wherein the copolymer further comprises a hydrophilic comonomer d), which comprises N-vinyllactam, (meth)acrylamide, poly(ethylene glycol) (meth)acrylate, an N—$C_{1-8}$ alkyl acrylamide, or mixtures thereof.

6. The composition according to claim 5, wherein the hydrophilic comonomer is a N-vinyllactam.

7. The composition according to claim 1, wherein the copolymer further comprises 5 to 70 wt % hydrophilic comonomer d).

8. The composition according to claim 1, wherein the copolymer comprises vinylimidazol and quaternized vinylimidazol, and wherein at least 20% of the vinylimidazol is converted to the quaternized vinylimidazol.

9. The composition according to claim 1, wherein the hydrophobic comonomer comprises mono $C_{12-20}$ alkyl terminated poly(ethylene glycol) (meth)acrylate.

10. The composition according to claim 1, wherein the dissolved salt comprises an ionic pesticide.

11. A method for preparing the composition as defined in claim 1 by mixing the pesticide and the copolymer.

12. A method for controlling phytopathogenic fungi and/or undesired plant growth and/or undesired attack by insects or mites and/or for regulating the growth of plants, where the composition as defined in claim 1 is allowed to act on the particular pests, their habitat or the plants to be protected from the particular pest, the soil and/or on undesired plants and/or the useful plants and/or their habitat.

13. The method of claim 12, wherein the acidic comonomer comprises a carboxylic acid unit, a sulfonic acid unit or a salt thereof.

14. The method of claim 12, wherein the acidic comonomer is acrylic acid or methacrylic acid.

15. The method of claim 12, wherein the copolymer comprises
    a) 20 to 80 wt % vinylimidazol or a quaternized vinylimidazol,
    b) 1 to 20 wt % acidic comonomer, and
    c) 1 to 25 wt % hydrophobic comonomer.

16. The method of claim 12, wherein the copolymer further comprises a hydrophilic comonomer d), which comprises N-vinyllactam, (meth)acrylamide, poly(ethylene glycol) (meth)acrylate, an N—$C_{1-8}$ alkyl acrylamide, or mixtures thereof.

17. The method of claim 16, wherein the hydrophilic comonomer is a N-vinyllactam.

18. The method of claim 12, wherein the copolymer further comprises 5 to 70 wt % hydrophilic comonomer d).

19. Seed treated with the composition of claim 1.

* * * * *